United States Patent [19]
Castellano

[11] Patent Number: 5,891,092
[45] Date of Patent: Apr. 6, 1999

[54] DISPOSABLE SAFETY SYRINGE AND METHOD OF MAKING THE SAME

[75] Inventor: Thomas P. Castellano, Carson City, Nev.

[73] Assignee: Visionary Medical Products Corporation, Los Angeles, Calif.

[21] Appl. No.: 942,836

[22] Filed: Oct. 2, 1997

[51] Int. Cl.$^6$ ...................................................... A61M 5/00
[52] U.S. Cl. .......................... 604/110; 604/198; 604/263
[58] Field of Search ................................... 604/110, 187, 604/192, 195, 198, 263

[56] References Cited

U.S. PATENT DOCUMENTS

| | | |
|---|---|---|
| 5,254,100 | 10/1993 | Huband . |
| 5,267,977 | 12/1993 | Feeney . |
| 5,279,584 | 1/1994 | Dillard, III et al. ................ 604/263 X |
| 5,330,430 | 7/1994 | Sullivan ............................. 604/198 X |
| 5,342,309 | 8/1994 | Hausser ............................. 604/198 X |
| 5,445,620 | 8/1995 | Haber et al. ....................... 604/110 X |
| 5,713,873 | 2/1998 | Jehle . |

*Primary Examiner*—John D. Yasko
*Attorney, Agent, or Firm*—Pillsbury Madison & Sutro LLP

[57] ABSTRACT

A medication delivery device for delivering medication using a piercing member. The medication delivery device includes a housing, a piercing member holder, a delivery actuator and a sealing diaphragm. The housing is for holding medication to be delivered, and includes a piercing member end and a delivery actuator end. The piercing member holder is coupled to the housing at the piercing member end and is adapted to secure the piercing member to the housing. The piercing member holder includes a sealing member that contacts the housing, a slideable protective cover coupled to the sealing member that slides over and contains the piercing member after a delivery of medication is delivered, and a disabling member for holding the piercing member, which is coupled to the housing at the piercing member end and configured to contact the sealing member to form a sealed passage for medication contained in the housing. The delivery actuator member is coupled to the delivery actuator end of the housing and adapted to expel the medication from the housing. The sealing diaphragm is coupled to one end of the delivery actuator to minimize contact of the medication with the delivery actuator and to substantially prevent leakage of medication through the delivery actuator. As an injection is completed, the disabling member of the piercing member holder contacts the sealing diaphragm and breaks it so that it is rendered incapable of performing future injections, and the delivery actuator member displaces the sealing member of the piercing member holder to slide the slidable cover over the piecing member to cover the piercing member and render it incapable of performing future injections.

13 Claims, 4 Drawing Sheets

DISPOSABLE SAFETY SYRINGE AND METHOD OF MAKING THE SAME

FIELD OF THE INVENTION

This invention relates to syringes and, in particular embodiments, to a disposable syringe that has improved disabling and safety characteristics.

BACKGROUND OF THE INVENTION

Traditionally, disposable "one-time use" syringes have been the most prevalently used devices worldwide for invasive delivery of medication. However, because the syringe is an invasive device, after a use on a patient, the syringe's needle may become a deadly transmitter of infectious diseases, such as Acquired Immune Deficiency Syndrome (AIDS), hepatitis or the like. Thus, syringes present a growing and ever present health hazard to patient care givers and patients in either institutional or home use settings. In addition, used, discarded syringes pose a real threat to anyone coming in contact with them.

It is also noted that conventional disposable one-time use syringes have often been associated with illicit drug users, who administer multiple injections from the same needle. This practice causes cross-contamination and results in the rapid spread of infectious diseases among these users.

In the past, to overcome these dangers, safe disposal of used syringes has been left entirely up to either the patient care giver or the patient. For example, conscientious disposal of syringes entails an elaborate and often dangerous procedure. First, the needle point is manually broken with a specially designed device; then, the syringe and the needle are separately disposed of in a special canister designed for safe storage and transportation of contaminated waste products. However, this procedure provides numerous opportunities for contact with a used syringe and increases the chance of being accidentally stuck by potentially contaminated needles. Also, the special canister itself, once filled with exposed needle points and used syringes, is itself a health and safety hazard.

Because of the past difficulties in safely handling, disposing and destroying used syringes, a growing number of health care professionals and other individuals have been infected by contaminated body fluids through accidental punctures and scratches from these dangerous devices. For this reason, patient care givers have been extremely vulnerable to and fearful about contracting a variety of infectious diseases from accidental needle injury.

In addition to the risk from needle sticks by legitimate drug users, disposable syringes are the most prevalent device for administering illicit drugs by drug abusers. Typically, in these situations, each single-use syringe will be used to administer multiple injections, and it is not unusual for a single syringe to be employed by more than one individual.

SUMMARY OF THE DISCLOSURE

It is an object of an embodiment of the present invention to provide an improved disposable safety syringe, which obviates for practical purposes, the above-mentioned limitations.

According to an embodiment of the invention, a medication delivery device for delivering medication uses a piercing member. The medication delivery device includes a housing, a piercing member holder, a delivery actuator and a sealing diaphragm. The housing is for holding medication to be delivered and includes a piercing member end and a delivery actuator end. The piercing member holder is coupled to the housing at the piercing member end and is adapted to secure the piercing member to the housing. The piercing member holder includes a sealing member that contacts the housing, a slideable protective cover coupled to the sealing member that slides over and contains the piercing member after a delivery of medication is delivered, and a disabling member for holding the piercing member, which is coupled to the housing at the piercing member end and configured to contact the sealing member to form a sealed passage for medication contained in the housing. The delivery actuator member is coupled to the delivery actuator end of the housing and adapted to expel the medication from the housing. The sealing diaphragm is coupled to one end of the delivery actuator to minimize contact of the medication with the delivery actuator and to substantially prevent leakage of medication through the delivery actuator. As an injection is completed, the disabling member of the piercing member holder contacts the sealing diaphragm and breaks it so that it is rendered incapable of performing future injections, and the delivery actuator member displaces the sealing member of the piercing member holder to slide the slidable cover over the piercing member to cover the piercing member and render it incapable of performing future injections.

In preferred embodiments, the medication delivery device is a syringe, the piercing member is a needle, and the actuator member is a plunger rod. The needle is inserted under the skin to deliver medication, and medication is delivered by axial displacement of the plunger rod in the housing towards the piercing member holder. Also, the plunger rod is hollow and the disabling member is a spear-like member that ruptures the sealing diaphragm covering the plunger rod. Further, the sealing member is formed from an elastic material having an axial bore, the disabling member is a spear-like member also having a bore and holding the needle, and wherein the axial bore of the sealing member and the disabling member bore provide a passage way for medication to be delivered from the housing to the needle.

In particular embodiments, the slidable protective cover is connected to the sealing member by a friction fit, and the sealing member has an axial bore to permit passage around the disabling member. Thus, when an injection is completed, the sealing member is axially displaced by the plunger rod to move the protective cover over the needle to render the needle unusable for future injections.

In further embodiments, the slidable protective cover may be omitted and the medication delivery device is disabled by rupturing the sealing diaphragm coupled to the one end of the delivery actuator. Alternatively, the sealing diaphragm may remain intact during and after an injection and the medication delivery device is disabled by covering the piercing member with the slidable protective cover.

Other features and advantages of the invention will become apparent from the following detailed description, taken in conjunction with the accompanying drawings which illustrate, by way of example, various features of embodiments of the invention.

BRIEF DESCRIPTION OF THE DRAWINGS

A detailed description of embodiments of the invention will be made with reference to the accompanying drawings, wherein like numerals designate corresponding parts in the several figures.

DETAILED DESCRIPTION OF THE PREFERRED EMBODIMENTS

Figure 7:
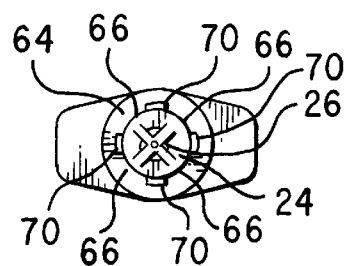
FIG. 7 is another exterior view of a needle holder used with the embodiment of FIG. 1.
Figure 2:
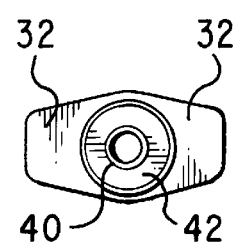
FIG. 2 is an end exterior view of the disposable safety syringe shown in FIG. 1.
Figure 1:
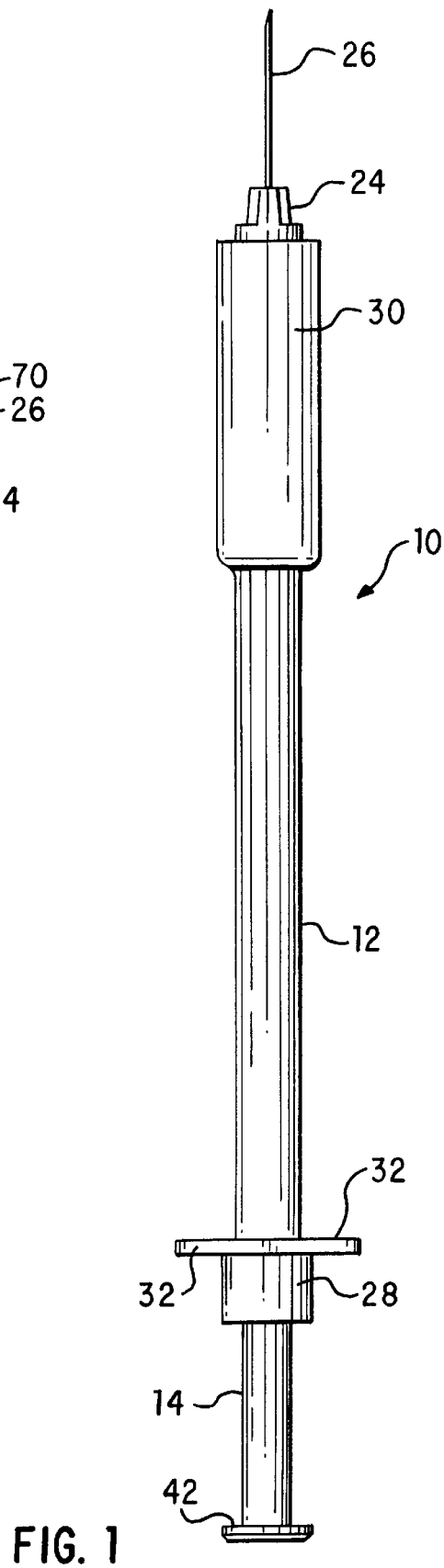
FIG. 1 is a side exterior view of a disposable safety syringe in accordance with an embodiment of the present invention.
Figure 3:
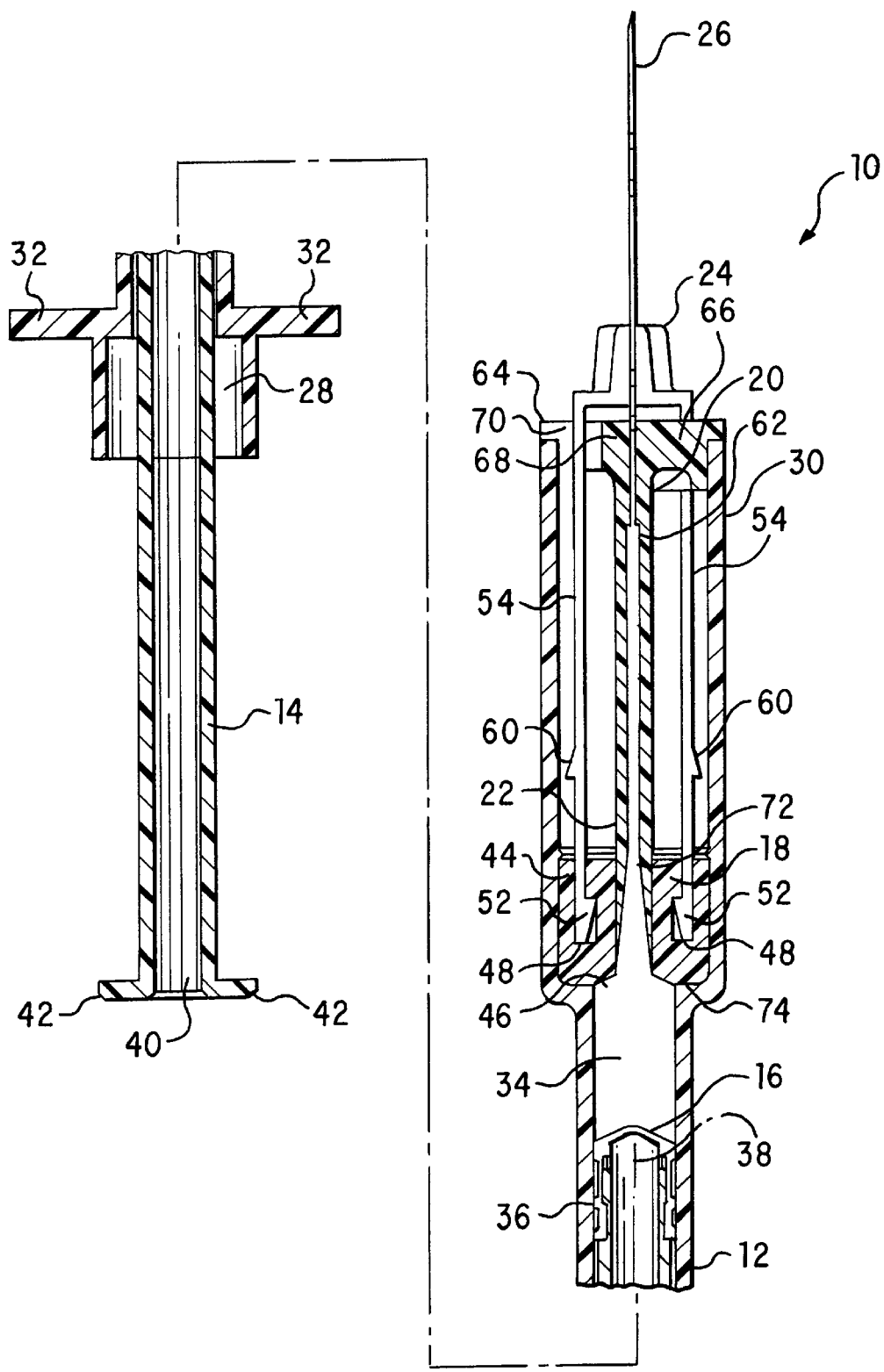
FIG. 3 is a cross-sectional view of the disposable safety syringe of FIG. 1 containing medication for an injection.
Figure 4:
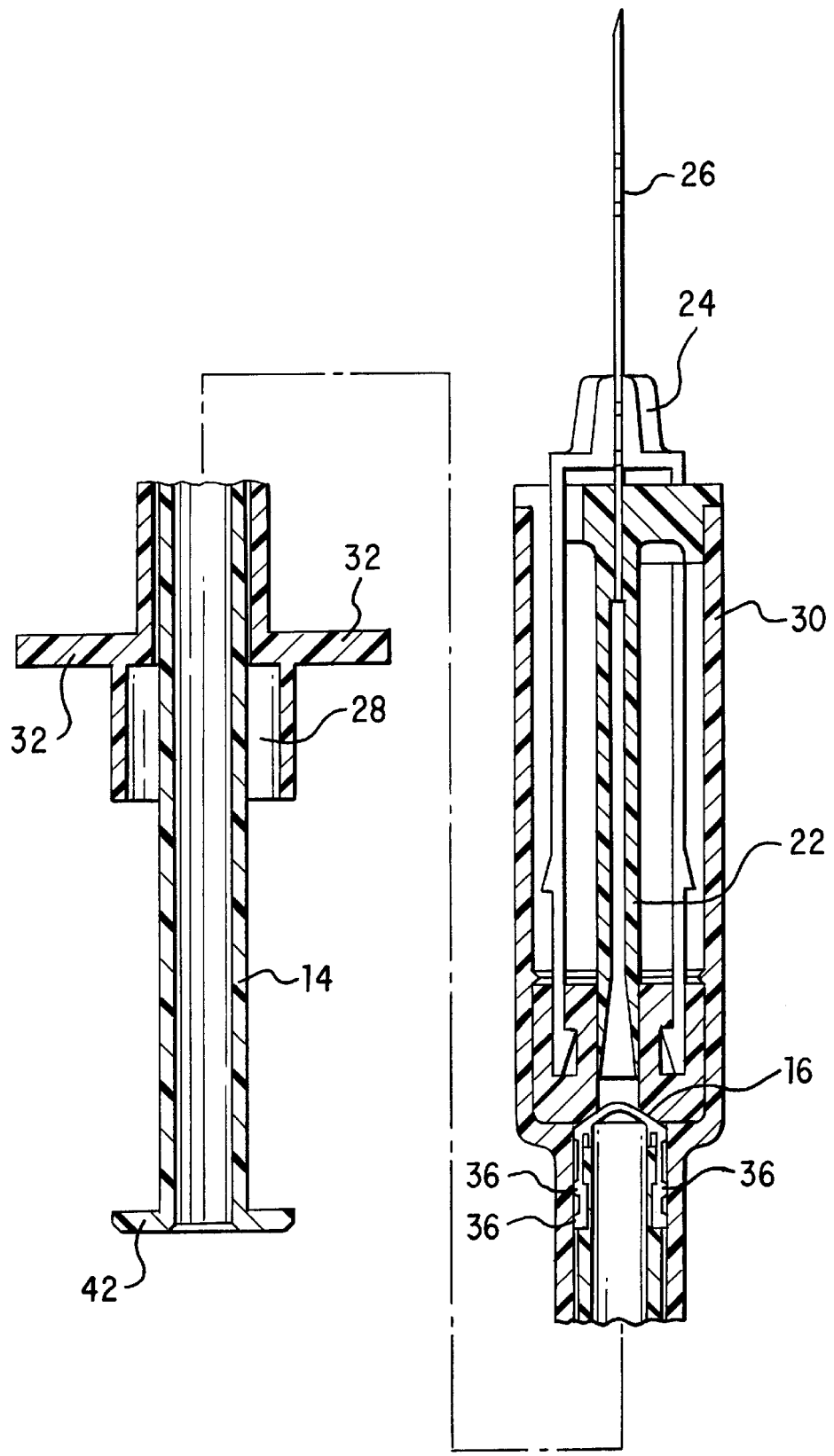
FIG. 4 is a cross-sectional view of the disposable safety syringe of FIG. 1 after completion of an injection and prior to disabling.

As shown in the drawings for purposes of illustration, the invention is embodied in a disposable safety syringe. In preferred embodiments of the present invention, the disposable safety syringe is loaded with medication, used for an injection and then discarded. However, it will be recognized that further embodiments of the invention may be used with pre-filled syringes or other invasive injection devices that utilize sharp invasive implements, piercing members, or the like for delivering substances into the body.

Embodiments of the present invention provide a relatively "passive" system for disabling a used syringe and safeguarding a needle from re-use and accidental contact with a patient or caregiver after an injection. The disposable safety syringe utilizes an essentially continuous stroke for disabling and enclosing a needle on the disposable syringe, which does not rely on an entire range of complex human activity. The use of a continuous stroke increases compliance with bio-hazard disposal protocols to improve public safety in general and to aid in the control of infectious diseases. Use of the disabling feature of these safety syringes, for legitimate medical purposes after a single use, helps prevent the syringes from becoming available for illegal purposes (such as IV drug abuse and the like). Thus, embodiments of the safety syringe are primarily directed to a safety improvement in disposable fixed needle syringes that utilize a self-encapsulating needle coupled with a self-disabling plunger to effectively eliminate the dangers of cross-contamination through accidental needle sticks or the possibility of a second injection being given with a used syringe. Preferably, after an injection of medication, the forward motion of this safety syringe's plunger is continued, and a permanent, non-removable protective cover slips over and encloses the needle point while simultaneously destroying the syringe by piercing the plunger diaphragm so that is can no longer be used to displace medication. Therefore, embodiments of the syringe operate reliably and efficiently to provide protection from syringe re-use as well as from accidental needle sticks.

Generally, embodiments of the safety syringe can be manufactured in all of the present disposable syringe sizes and may be useable for a variety of medical capacities, with various needle gauges, and for different medication applications.

A disposable safety syringe 10 in accordance with an embodiment of the present invention is shown in FIGS. 1–5. The syringe 10 includes a housing 12, a plunger 14, a plunger diaphragm 16, a sealing gasket 18, a needle holder 20 including a spear-like member 22, a slideable protective cap 24, and a needle 26.

In preferred embodiments, the housing 12 is manufactured from a clear polymer material that is certified for use in medical devices and syringes. During the initial stage of manufacturing, the housing 12 is injection molded with both ends of the housing 12 being open to facilitate proper sterilization and later assembly. In alternative embodiments, the housing 12 may be formed out of other materials, such as plastic, glass, metal, composites, a combination of materials, and the like, and may be formed by casting or die striking, or from multiple pieces that are either snap fitted or adhered together, or the like.

The housing 12 has a plunger end 28 for receiving the plunger 14 and a piercing member end 30 for receiving the needle 26 and other members associated with the needle 26. At the plunger end 28 of the housing 12, there are integral finger supports 32 that are used to stabilize the syringe 10 during medication delivery. The exterior of the plunger portion 28 of the housing 12 includes radial markers that are graduated for accurate measurement of medication. The radial markers may also contain numbers which indicate fractional amounts of a CC or multiple CCs, depending on the size of the syringe and its medical application. In alternative embodiments, different markers or marking methods may used to accurately indicate the amount of medication contained in the syringe 10. An axial bore 34 is located through a centerline of the housing 12 extending from the plunger end 28 to the piercing member end 30 to contain measured amounts of medication. The axial bore 34 is also adapted to accept the plunger diaphragm 16 attached to the plunger 14 with a slight interference fit (created by the raised sealing rings 36) facilitating a proper seal to prevent or substantially reduce medication leakage during draw-up of medication and during delivery. The piercing member end 30 of the housing 12 is expanded in diameter relative to the plunger end 28 to contain the sealing gasket 18, the slideable protective cover or sheath 24 and the needle holder that includes the plunger diaphragm piercing device or spear-like member 22 that holds the needle 26. In alternative embodiments, the piercing member end 30 may be of a larger or smaller diameter, compared to the plunger end 28, with the relative size dependent on the size of the needle, protective cover, the size of the syringe and/or the environment in which the syringe will be used.

In accordance with the embodiment of FIGS. 1–5, the plunger 14 is a hollow tube with one end 38 covered by the pierceable plunger diaphragm 16. The other end 40 of the plunger 14 includes enlarged finger rests 42 to provide stability and facilitate medication delivery when pushing the plunger 14 towards the piercing member end 30 of the housing 12. Once the end 38 is covered by the plunger diaphragm 16, the plunger 14 can be used to push the medication through the axial bore 34 of the housing 12 of the syringe 10. Preferably, the plunger 14 is manufactured from a semi-rigid polymer material which is certified for use on medical devices. However, in alternative embodiments, other materials such as plastics, glass, ceramics, metal, composites, or the like may be used. In addition, it is preferred that the end 40 is also open and connected to the end 38 of the hollow plunger 14 to further facilitate disabling of the syringe once the plunger diaphragm 16 is ruptured. This will allow medication to escape through the hollow plunger 14. However, in alternative embodiments, the end 40 may be closed off, and the hollow plunger may be open at end 38 to the interior of the hollow plunger, such that the hollow plunger 14 is only hollow for a sufficient length to permit rupturing of the plunger diaphragm 16. In further embodiments, the interior of the hollow plunger 14 is formed with barbs, or the like (not shown), to engage and lock the plunger 14 to the spear-like member 22 after the spear-like member 22 has ruptured the plunger diaphragm 16. In still further embodiments of the present invention, the hollow plunger rod may be formed with additional locking tabs, barbs, or the like (not shown) formed near the enlarged finger rests 42 to lock the plunger 14 into the housing 12 once the disabling continuous stroke is completed.

In preferred embodiments, the plunger diaphragm 16 is an elastic cap that fits over the end 38 of the hollow plunger 14 to close off and seal the end 38 of the hollow plunger 14. In addition, the exterior surface of the plunger diaphragm 16 includes sealing rings 36 to provide a leak resistant seal between the plunger 14 and the interior of the axial bore 34 of the housing 12, which contains the medication. The plunger diaphragm 16 is pierceable by a push through detent needle, awl, or the spear-like member 22 that ruptures or tears the plunger diaphragm 16 after an injection to prevent the syringe 10 and the plunger diaphragm 16 from being utilized for future injections. Generally, the plunger diaphragm 16 is secured to the plunger 14 prior to final assembly and insertion into the axial bore of the plunger end 28 of the housing 12. In preferred embodiments, the plunger diaphragm 16 is formed from a molded elastic material, and is either glued on, snap fitted or secured by friction to the plunger 14. The plunger diaphragm is a molded product which is manufactured from a material that is certified for use in this type of medical device. In preferred embodiments, the plunger diaphragm is made of rubber. However, in alternative embodiments, the plunger diaphragm may be formed from plastic, polymers, foils, composites or other elastic materials.

A soft pliable sealing gasket 18 is placed inside the piercing member end 30 of the housing 12 such that the sealing gasket 18 is in contact with the sides 44 of the piercing member end 28 to prevent or substantially reduce leakage of medication around the sealing gasket 18 during draw-up or an injection of medication. In preferred embodiments, the portion of the sealing gasket 18 that faces the axial bore 34 of the housing 12 includes a sealing ring to ensure proper sealing during draw-up and delivery of medication. The sealing gasket 18 also includes an axial bore 46 to form a part of a passage for a medication contained in the axial bore 34 of the housing 12 that is to be delivered to the needle 26. In preferred embodiments, the bore 46 is tapered to facilitate guidance of medication to the needle 26 and to handle hydraulic loads created during an injection better. However, other bore shapes and diameters may be used, with the choice being dependent on the size of the syringe, the type of medication, the size of the needle, and/or the like. The axial bore 46 is also used to form a substantially leak-proof seal with the spear-like member 22.

The sealing gasket 18 has a circular recess 48, which is located and formed on a face 50 of the sealing gasket 18 that faces the spear-like member 22. The circular recess 48 is shaped to accept and retain gripping members 52 on the end of the slidable protective cap 24. In preferred embodiments, the sealing gasket 18 has an outer diameter near the face 50 that is slightly undersized from the inner diameter of the piercing member end 30 of the housing 12. This allows for displacement of the sealing gasket 18 during the continuous stroke associated with the displacement of the slideable protective cap 24 over the needle 26 which is carried out simultaneously with the puncturing the plunger diaphragm 16. In alternative embodiments, the sealing gasket 18 may use a segmented recess or have an outer diameter that is equal to or larger than the piercing member end 30 of the housing 12.

Figures 5, 6:
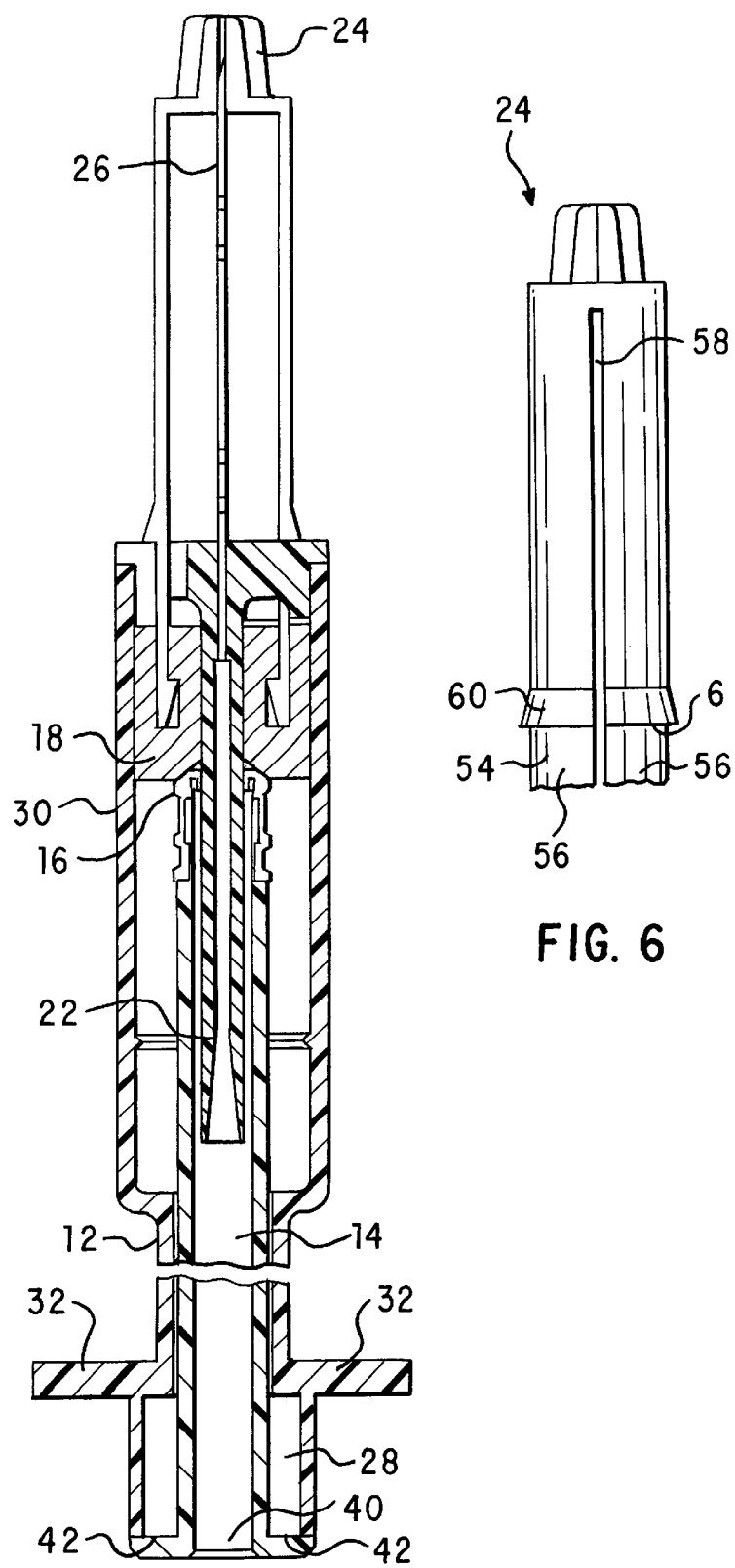
FIG. 5 is a cross-sectional view of the disposable safety syringe of FIG. 1 after the syringe is disabled.
FIG. 6 is a side exterior view of a slidable protective cap used with the embodiment of FIG. 1.

Preferably, the slideable protective cap 24 is manufactured from a polymer which is certified for use in this type of medical device. However, in alternative embodiments, other suitable medical materials such as plastics, composites, metal, or the like may be used. As shown in FIG. 6, the slidable protective cap 24 is generally cylindrical in shape and segmented around the diameter of the slidable protective cap 24 to form one or more protective panels 54 having ends 56 forming a slot 58 to permit assembly of the various components and to act as a guide for the slidable protective cover 24 as it covers the needle 26 after completion of an injection. In preferred embodiments, there are four protective panels 54; however, in alternative embodiments, there may be one protective panel 54 and slot 58 or there may be a greater number of protective panels and slots with the number being dependent on the size of the syringe 10 and the materials that the slidable protective cap 24 and needle holder 20 are formed from. The slideable protective cover 24 includes the gripping members 52 at the end and on the inner surface of the protective panels 54, which are used to grip and secure the slidable protective cap 24 to the sealing gasket 18. The slidable protective cap 24 also includes locking members 60 on the exterior surface of the protective panels 54, which are used to lock the slidable protective cover 24 to the top and sides of the needle holder 20 after completion of an injection. In preferred embodiments, the gripping members 52 and the locking members 60 extend around the inner and outer circumference, respectively, of each protective panel 54. However, in alternative embodiments, the gripping members 52 and locking members 60 may be formed as short discrete tabs, nubs, teeth or the like. In preferred embodiments the gripping members 54 and locking members 60 have a triangular cross-section to secure the members to the sealing gasket and top and sides of the needle holder 20. However, in alternative embodiments, other cross-sections may be used to provide the locking and gripping functions.

As shown in FIG. 7, the end of the needle holder 20 includes a needle bore 62 for securing the needle 26 and for providing a passage for the medication to travel through the spear-like member 22 to the needle 26 during an injection. Preferably, the top of the needle holder 20 has sides 64 around the outer diameter of the needle holder 20, and one or more spokes 66 extending from the sides 64 to a center support 68 of the needle holder 20 containing the needle bore 62. The area between the sides 64, spokes 66 and center support 68 forms ports 70 that permit the protective panels 54 of the slidable protective cap 24 to be inserted and slid down during assembly and to be slid up during the continuous stroke that disables the syringe 10 after an injection. In preferred embodiments, the top of the needle holder 20 includes four spokes 66 and four ports 70. However, in alternative embodiments, the top of the needle holder 20 may include as little as one spoke and one large port 70 or more spokes and ports with the number being dependent on the size of the syringe 10 and the materials from which the needle holder 20 and slidable protective cap 24 are formed.

Attached to an underside of the center support 68 of the needle holder 20 is the spear-like member 22 that provides for fluid transfer to the needle 26, ruptures the plunger diaphragm 16 after an injection and assists in retaining the needle 26. Preferably, the needle holder 20 and the spear-like member 22 are formed as a single, integral piece from a "hard" polymer that is certified for use in this type of medical device. However, in alternative embodiments, the needle holder 20 and spear-like member may be formed from multiple parts and formed from other suitable medical materials, such as plastics, metal, glass, ceramics, composites, or the like. An end 72 of the spear-like member 22 mates with the internally tapered bore 46 of the sealing gasket 18 to provide a leak-proof or resistant seal with the housing 12 to provide a passage for the medication to be transferred from the housing 12 to the needle 26 during an injection. As discussed above, the end 72 of the spear-like member 22 is used to puncture or rupture the plunger diaphragm 16 when the user of the syringe has completed the medication injection delivery stroke. In preferred embodiments, the spear-like member is smooth to slide easily through the bore 34 of the sealing gasket 18 and the hollow plunger 14 after piercing the plunger diaphragm 16. However, in alternative embodiments, the spear-like member 22 may include ridges or barbs that resist attempts to reset the syringe 10, once the disabling procedure has begun.

Disabling of the syringe 10 is accomplished by a continuous stroke after completion of an injection. The rupturing of the plunger diaphragm 16 is accomplished by a continued push through linear motion (e.g., the continuous stroke) of the plunger 14 at the end of the medication delivery stroke. This motion simultaneously pushes the end 72 through the bore 46 of the sealing gasket 18, through the plunger diaphragm 16 and into the hollow plunger 14. The spear-like member 22 also acts as a directional guide for the sealing gasket 18 and the slidable protective cap 24 as it slides to cover the needle 26. As the slidable protective cap 24 moves to cover the needle 26, the locking members 60 on the exterior of the protective panels 54 of the slidable protective cap 24 slide past the sides 64 of the top of the needle holder 20, and then the locking members 60 move outward to engage the top surface of the sides 64 of the needle holder 20 to prevent the slideable protective cap 24 from being pressed back into the piercing member end 30 of the housing 12 to re-expose the needle 26. Locking the slidable protective cap 24 in position also guards against accidental retraction of the slidable protective cap 24 during handling of the disabled syringe 10. In further embodiments, the completion of the continuous disabling stroke locks a portion of the hollow plunger 14 inside the axial bore 34 of the housing 12 near the plunger end 28 to prevent the plunger 14 from being withdrawn from the disabled device.

To assemble the syringe 10, the end 38 of the plunger 14 is covered with the plunger diaphragm 16 to prepare the plunger 14 for insertion in the plunger end 28 of the housing 12. At this point, the plunger 14 may be inserted in the plunger end 28 of the housing 12 or may be inserted at the completion of the assembly process. Next, a needle 26 is secured in the needle bore 62 of the center support 68 in the top of the needle holder 20. However, in alternative embodiments, the needle 26 may be coupled to the needle bore 62 at the completion of the assembly of the sealing gasket, the needle holder 20 and the slideable protective cap 24. Then the protective panels 54 of the slidable protective cap 24 are slid through the corresponding ports 70 in the top of the needle holder 20. To facilitate passing the protective panels through the posts 70 and to avoid the locking members 60 from engaging with the sides 64 of the top of the needle holder 20, the protective panels 54 are preferably bent inward towards the center support 68 to provide sufficient clearance of the locking members 60. Once the slidable protective cap 24 is slid all the way down, until the end of the slidable protective cap 24 contacts the top of the needle holder 20, the sealing gasket is pressed against the end 72 of the spear-like member 22 and the gripping members 52 of the slidable protective cap 24. The sealing gasket 18 is then pressed to engage the end 72 of the spear-like member 22 in the bore 46 and to position the gripping members 52 in the recess 50 to secure the sealing gasket 18, needle holder 20 and slideable protective cap together as a unit. It should be noted that once the gripping members 52 of the protective panels 54 are secured in the recess of the sealing gasket 18, it is difficult to bend the protective panels 54 sufficiently inward to permit the locking members 60 to pass back over the sides 64 of the top of the needle holder 20 after the syringe 10 is disabled. At this point, the entire assembly of the sealing gasket 18, the needle holder 20 and the slidable protective cap 24 are inserted and slid into the piercing member end 30 of the housing 12 until the sealing gasket 18 contacts an end 74 of the housing 12. The top of the needle holder 20 is then spot welded, glued, snap fitted, or otherwise secured by a procedure acceptable for medical device, to the walls 44 of the piercing member end of the housing to secure the assembly in position. If a needle 26 has not yet been mounted in the needle bore 62, it is attached at the post. Once it is attached, the needle 26 and assembly are sterilized and a protective cover is attached to the housing 12 or the top of the needle holder 20 to maintain sterilization and protect the needle 26 during transport. In alternative embodiments, the protective cover 100 (not shown) can be secured to the end of the slidable protective cap 24 if it can be removed without pulling the slidable protective cap 24 and the sealing gasket 18 forward. In preferred embodiments, the protective cap is secured by spot welding. However, in alternative embodiments gluing, snap fits or the like may be used.

If the plunger 14 has not yet been inserted in the plunger end 28 of the housing 12, the plunger 14 is inserted and slid until the plunger diaphragm 16 contacts the sealing gasket 18 at the end of the axial bore 34. Finally, the entire syringe is sterilized again and a protective end cap (not shown) is placed over the enlarged finger rests 42 to maintain sterilization and protect the plunger 14 from being depressed during transport. In preferred embodiments, the protective cap is secured by spot welding. However, in alternative embodiments gluing, snap fits or the like may be used. In preferred embodiments, the syringe 10 is assembled and sterilized using automated manufacturing processes. However, in alternative embodiments, the syringe 10 may be assembled by hand or by using a combination of hand and automated processes.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A medication delivery device for delivering medication with a piercing member, the medication delivery device comprising:

a housing for holding medication to be delivered, wherein the housing has a piercing member end and a delivery actuator end;

a piercing member holder is coupled to the housing at the piercing member end and is adapted to secure the piercing member to the piercing member end of the housing, the piercing member holder including:

a sealing member contacting the housing, a slideable protective cover coupled to the sealing member and to slide over and contain the piercing member after a delivery of medication is delivered, and a disabling member for holding the piercing member, wherein the disabling member is coupled to the housing and configured to contact the sealing member to form a sealed passage for medication contained in the housing;

a delivery actuator member coupled to the delivery actuator end of the housing and adapted to expel the medication from the housing; and a sealing diaphragm coupled to one end of the delivery actuator to minimize contact of the medication with the delivery actuator and to substantially prevent leakage of medication through the delivery actuator.

2. A medication delivery device according to claim 1, wherein as an injection is completed, the disabling member of the piercing member holder contacts the sealing diaphragm and breaks it to render it incapable of performing future injections, and the delivery actuator member displaces the sealing member of the piercing member holder to slide the slidable cover over the piecing member to cover the piercing member and render it incapable of performing future injections.

3. A medication delivery device according to claim 1, wherein the medication delivery device is a syringe, the piercing member is a needle, and the actuator member is a plunger rod, wherein the needle is inserted under the skin to deliver medication, and medication is delivered by axial displacement of the plunger rod in the housing towards the piercing member holder.

4. A medication delivery device according to claim 3, wherein the plunger rod is hollow and the disabling member is a spear-like member that ruptures the sealing diaphragm covering the plunger rod.

5. A medication delivery device according to claim 3, wherein the sealing member is formed from an elastic material having an axial bore, the disabling member is a spear-like member also having a bore and holding the needle, and wherein the axial bore of the sealing member and the disabling member bore provide a passageway for medication to be delivered from the housing to the needle.

6. A medication delivery device according to claim 3, wherein the slidable protective cover is connected to the sealing member by a friction fit, and wherein the sealing member has an axial bore to permit passage around the disabling member, and wherein when an injection is completed, the sealing member is axially displaced by the plunger rod to move the protective cover over the needle to render the needle unusable for future injections.

7. A medication delivery device for delivering medication with a piercing member, the medication delivery device comprising:

a housing for holding medication to be delivered, wherein the housing has a piercing member end and a delivery actuator end;

a piercing member holder is coupled to the housing at the piercing member end and is adapted to secure the piercing member to the piercing member end of the housing, the piercing member holder including:
a sealing member contacting the housing, and
a disabling member for holding the piercing member, wherein the disabling member is coupled to the housing and configured to contact the sealing member to form a sealed passage for medication contained in the housing;

a delivery actuator member coupled to the delivery actuator end of the housing and adapted to expel the medication from the housing; and a sealing diaphragm coupled to one end of the delivery actuator to minimize contact of the medication with the delivery actuator and to substantially prevent leakage of medication through the delivery actuator, wherein as an injection is completed, the disabling member of the piercing member holder contacts the sealing diaphragm and breaks it to render it incapable of performing future injections.

8. A medication delivery device according to claim 7, wherein the medication delivery device is a syringe, the piercing member is a needle, and the actuator member is a plunger rod, wherein the needle is inserted under the skin to deliver medication, and medication is delivered by axial displacement of the plunger rod in the housing towards the piercing member holder.

9. A medication delivery device according to claim 8, wherein the plunger rod is hollow and the disabling member is a spear-like member that ruptures the sealing diaphragm covering the plunger rod.

10. A medication delivery device according to claim 8, wherein the sealing member is formed from an elastic material having an axial bore, the disabling member is a spear-like member also having a bore and holding the needle, and wherein the axial bore of the sealing member and the disabling member bore provide a passage way for medication to be delivered from the housing to the needle.

11. A syringe for delivering medication with a needle, the syringe comprising:

a housing for holding medication to be delivered, wherein the housing has a needle end and a plunger end;

a needle holder is coupled to the housing at the needle end and is adapted to secure the needle to the needle end of the housing, the needle holder including:
a sealing member contacting the housing,
a slideable protective cover coupled to the sealing member and to slide over and contain the needle after a delivery of medication is delivered, and
a spear-like member for holding the needle, wherein the spear-like member is coupled to the housing and configured to contact the sealing member to form a sealed passage for medication contained in the housing;

a hollow plunger rod coupled to the plunger end of the housing and adapted to expel the medication from the housing; and a sealing diaphragm coupled to and covering one end of the plunger rod to minimize contact of the medication with the plunger rod and to substantially prevent leakage of medication through the plunger rod, wherein as an injection is completed, the spear-like member of the needle holder contacts the sealing diaphragm and breaks it to render it incapable of performing future injections, and wherein the plunger rod displaces the sealing member of the needle holder to slide the slidable cover over the needle to cover the needle and render it incapable of performing future injections.

12. A syringe according to claim 11, wherein the sealing member is formed from an elastic material having an axial bore, the spear-like has a bore and holds the needle, and wherein the axial bore of the sealing member and the spear-like member bore provide a passage way for medication to be delivered from the housing to the needle.

13. A syringe according to claim 3, wherein the slidable protective cover is connected to the sealing member by a friction fit, and wherein the sealing member has an axial bore to permit passage around the spear-like member, and wherein when an injection is completed, the sealing member is a axially displaced by the plunger rod to move the protective cover over the needle to render the needle unusable for future injections.

* * * * *